(12) United States Patent
Hoffmann-Clair et al.

(10) Patent No.: US 7,041,103 B2
(45) Date of Patent: May 9, 2006

(54) MULTIPIN CLAMP AND ROD ATTACHMENT

(75) Inventors: Mindy L. Hoffmann-Clair, Mohnton, PA (US); Michael C. Mazzio, Schwenksville, PA (US)

(73) Assignee: Synthes (USA), Paoli, PA (US)

(*) Notice: Subject to any disclaimer, the term of this patent is extended or adjusted under 35 U.S.C. 154(b) by 469 days.

(21) Appl. No.: 10/402,896

(22) Filed: Mar. 28, 2003

(65) Prior Publication Data

US 2003/0191467 A1   Oct. 9, 2003

Related U.S. Application Data

(63) Continuation of application No. PCT/US01/48836, filed on Dec. 13, 2001, and a continuation-in-part of application No. 09/736,753, filed on Dec. 14, 2000, now Pat. No. 6,565,564.

(51) Int. Cl.
*A61F 5/04* (2006.01)
(52) U.S. Cl. ........................................... 606/59
(58) Field of Classification Search ................. 606/54, 606/57–59
See application file for complete search history.

(56) References Cited

U.S. PATENT DOCUMENTS

| | | | |
|---|---|---|---|
| 1,997,466 A | 4/1935 | Longfellow | |
| 2,250,417 A | 7/1941 | Ettinger | |
| 2,346,346 A | 4/1944 | Anderson | |
| 2,362,957 A * | 11/1944 | Hackett | 606/86 |
| 2,391,537 A | 12/1945 | Anderson | |
| 2,391,693 A | 12/1945 | Ettinger | |
| 3,477,429 A * | 11/1969 | Sampson | 606/86 |
| 4,135,505 A | 1/1979 | Day | |
| 4,271,832 A | 6/1981 | Evans et al. | |
| 4,312,336 A | 1/1982 | Danieletto et al. | |
| 4,365,624 A | 12/1982 | Jaquet | |
| 4,411,259 A * | 10/1983 | Drummond | 606/61 |
| 4,483,334 A | 11/1984 | Murray | |
| RE31,809 E | 1/1985 | Danieletto et al. | |
| 4,502,473 A | 3/1985 | Harris et al. | |
| 4,535,763 A | 8/1985 | Jaquet | |
| 4,541,422 A | 9/1985 | de Zbikowski | |
| 4,620,533 A | 11/1986 | Mears | |
| 4,621,627 A | 11/1986 | DeBastiani et al. | |
| 4,628,919 A | 12/1986 | Clyburn | |

(Continued)

FOREIGN PATENT DOCUMENTS

DE   299 22 734 U1   3/2000

(Continued)

*Primary Examiner*—Eduardo C. Robert
*Assistant Examiner*—Mary C. Hoffman
(74) *Attorney, Agent, or Firm*—Jones Day

(57) ABSTRACT

A simplified external bone fixator assembly is provided which allows the surgeon to snap a bone fixation rod into the assembly at any location along the length of the rod. The invention does not require "threading" of the assembly onto the rod starting at the end and sliding it down the length of the rod to the desired location. In particular, a bone pin locking assembly is provided for use with standard bone fixation rods and bone pins. The assembly includes a bone pin vise, a single-piece fixation rod attachment member and a coupling to allow relative adjustment of pin vise and rod attachment member. The single-piece rod attachment member has two opposing jaws that loosely capture the bone fixation rod when the surgeon presses the rod into the attachment member. The assembly may be rigidly fixed to the rod using a bolt which tightens the attachment member onto the rod.

31 Claims, 10 Drawing Sheets

U.S. PATENT DOCUMENTS

| | | |
|---|---|---|
| 4,628,922 A | 12/1986 | Dewar |
| 4,714,076 A | 12/1987 | Comte et al. |
| 4,922,896 A | 5/1990 | Agee et al. |
| 4,941,481 A | 7/1990 | Wagenknecht |
| 4,988,349 A | 1/1991 | Pennig |
| 5,053,034 A | 10/1991 | Olerud |
| 5,056,198 A * | 10/1991 | Viglione ..................... 24/336 |
| 5,098,432 A | 3/1992 | Wagenknecht |
| 5,108,394 A | 4/1992 | Kurokawa et al. |
| 5,152,280 A | 10/1992 | Danieli |
| 5,160,335 A | 11/1992 | Wagenknecht |
| 5,207,676 A | 5/1993 | Canadell et al. |
| 5,219,349 A | 6/1993 | Krag et al. |
| 5,292,322 A | 3/1994 | Faccioli et al. |
| 5,320,622 A | 6/1994 | Faccioli et al. |
| 5,320,623 A | 6/1994 | Pennig |
| 5,342,360 A | 8/1994 | Faccioli et al. |
| 5,376,090 A | 12/1994 | Pennig |
| RE34,985 E | 6/1995 | Pennig |
| 5,454,810 A | 10/1995 | Pohl et al. |
| 5,624,440 A | 4/1997 | Huebner |
| 5,630,815 A | 5/1997 | Pohl et al. |
| 5,658,283 A | 8/1997 | Huebner |
| 5,662,648 A | 9/1997 | Faccioli et al. |
| 5,662,650 A | 9/1997 | Bailey et al. |
| 5,683,389 A | 11/1997 | Orsak |
| 5,709,681 A | 1/1998 | Pennig |
| 5,709,685 A | 1/1998 | Dumbrowski et al. |
| 5,728,096 A | 3/1998 | Faccioli et al. |
| 5,741,252 A | 4/1998 | Mazzio et al. |
| 5,746,741 A | 5/1998 | Kraus et al. |
| 5,752,954 A | 5/1998 | Mata et al. |
| 5,788,695 A | 8/1998 | Richardson |
| 5,827,282 A | 10/1998 | Pennig |
| 5,827,283 A | 10/1998 | Groiso et al. |
| 5,891,144 A | 4/1999 | Mata et al. |
| 5,897,555 A | 4/1999 | Clyburn et al. |
| 5,921,985 A | 7/1999 | Ross, Jr. et al. |
| 5,941,879 A | 8/1999 | Walulik et al. |
| 5,954,725 A | 9/1999 | Sherman et al. |
| 5,961,515 A | 10/1999 | Taylor et al. |
| 5,989,250 A * | 11/1999 | Wagner et al. ................. 606/61 |
| 6,022,348 A | 2/2000 | Spitzer |
| 6,024,745 A | 2/2000 | Faccioli et al. |
| 6,080,153 A | 6/2000 | Mata et al. |
| 6,277,119 B1 | 8/2001 | Walulik et al. |
| 6,342,054 B1 | 1/2002 | Mata |
| 6,482,206 B1 | 11/2002 | Schoenefeld |
| 6,513,775 B1 * | 2/2003 | Hostetler .................... 248/304 |
| 6,565,564 B1 | 5/2003 | Hoffman et al. |
| 6,613,049 B1 * | 9/2003 | Winquist et al. ............... 606/59 |
| 6,652,523 B1 * | 11/2003 | Evrard et al. ................. 606/54 |
| 6,702,814 B1 * | 3/2004 | Walulik et al. ............... 606/57 |

FOREIGN PATENT DOCUMENTS

| | | |
|---|---|---|
| WO | WO/0038585 | 7/2000 |

* cited by examiner

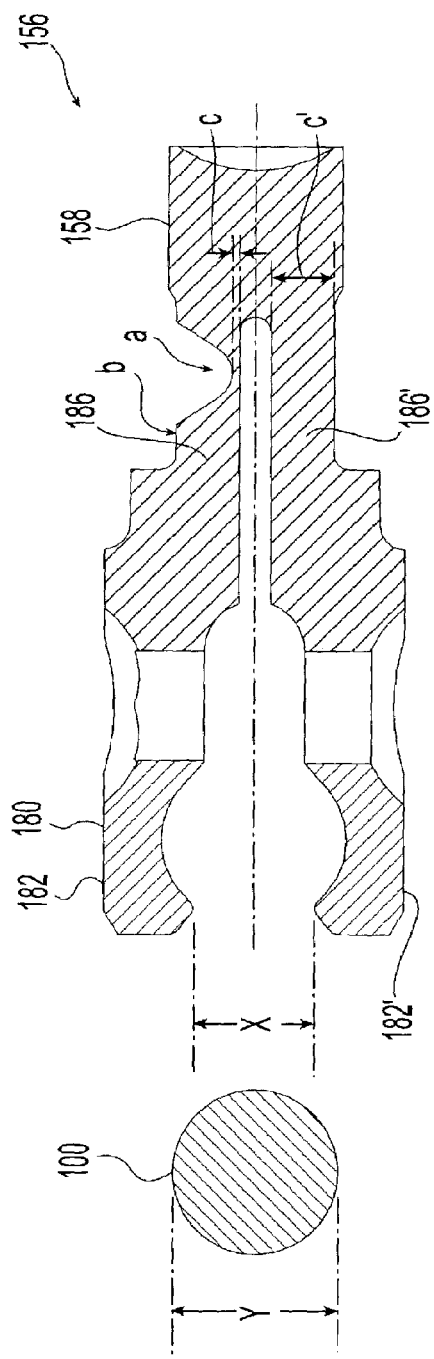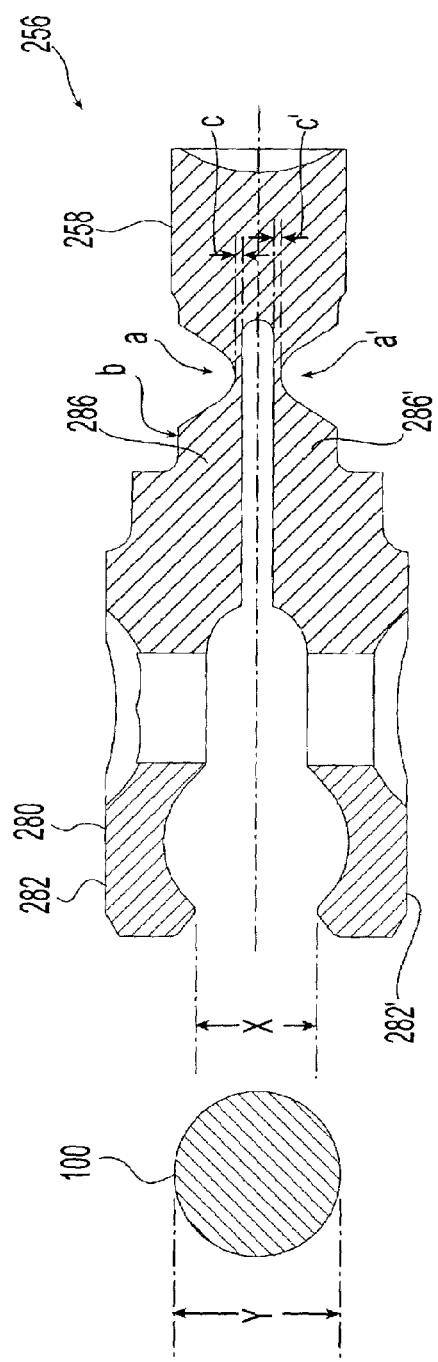
Fig. 5b
Fig. 5c

MULTIPIN CLAMP AND ROD ATTACHMENT

CROSS-REFERENCE TO RELATED APPLICATIONS

This application is a continuation of the US National Phase designation of co-pending international patent application number PCT/US01/48836, filed Dec. 13, 2001; and is a continuation-in-part of U.S. nonprovisional patent application Ser. No. 09/736,753, filed Dec. 14, 2000 now U.S. Pat. No. 6,565,564; the entire content of which applications is expressly incorporated herein by reference thereto.

TECHNICAL FIELD

The present invention relates to a traumatologic device, and, more particularly, to an improved traumatologic device for reducing long-bone fractures that require external fixation.

BACKGROUND OF THE INVENTION

A variety of traumatologic devices for reduction of bone segments are known in the art. For example external bone fixation devices (commonly referred to as external fixators) are known. Typically external fixators are used to reduce fractures of the long bones in the human body. These devices are placed in position under anesthesia. In order to reduce the duration of the anesthesia, fixator devices have been developed to allow positioning at every possible angle, while still allowing easy adjustment by a surgeon.

Devices designed to the present day generally fix the bone pin clamp to the bone fixation rod by way of a closed hole and screw combination, or by using two-piece open face bone fixation rod jaws which by their nature cannot be self-sprung and so require the use of an additional piece or pieces, such as a coil or compression spring, to maintain the jaws in an open position during installation onto the bone fixation rod. The two piece nature of such designs increases unit fabrication difficulty and cost.

Accordingly, there is a need in the art to provide a simpler bone pin clamp assembly that makes it easier for an operator to engage the clamp assemblies and bone fixation rod, while still providing maximum flexibility to the operator in adjusting the distance between bone pin clamps on either side of a fracture.

SUMMARY OF THE INVENTION

The present invention provides a fixation rod clamp for coupling a bone pin locking assembly to a bone fixation rod. The clamp may comprise a single-piece rod attachment member having a longitudinal axis, a jaw portion having first and second opposing jaws configured to receive the bone fixation rod, the first opposing jaw having a first spring constant and the second opposing jaw having a second spring constant, where the first and second spring constants are unequal. The rod attachment member may further comprise a coupling portion. The fixation rod clamp may further comprise a coupling having a pin vise cooperating portion to engage the bone pin locking assembly and also configured to receive the coupling portion of the rod attachment member. The jaw portion of the rod attachment member may be configured to engage the bone fixation rod when the rod is pressed into the opposing jaws to mechanically couple the bone pin locking assembly to the bone fixation rod.

The fixation rod clamp may be configured such that when at least one of the first and second opposing jaws is displaced from a rest position, a resulting spring force is generated in the at least one jaw which forces the jaw back to the rest position. The fixation rod clamp may also be configured such that when the bone fixation rod is pressed into the rod attachment member the first and second jaws are displaced an unequal amount. The fixation rod clamp may also be configured such that when the bone fixation rod is pressed into the rod attachment member the first jaw is displaced from its rest position and the second jaw remains substantially stationary.

The first and second jaws of the fixation rod clamp may have a clearance therebetween sufficient to provide an interference between the opposing jaws and the bone fixation rod when the rod is pressed into the clamp jaw portion.

The fixation rod clamp may further have a locked position that substantially prevents movement of the clamp along the bone fixation rod. A bolt may be disposed within, and operatively associated with, the fixation rod clamp jaw portion, so that tightening of the bolt configures the clamp to the locked position.

The fixation rod clamp jaw portion may be configured to engage the bone fixation rod when the rod is pressed into the jaw portion in a direction substantially along the longitudinal axis of the rod attachment member.

The pin vise cooperating portion of the coupling may comprise a bearing face incorporating serrations configured to cooperatively engage serrations in the bone pin locking assembly, the serrations configured to prevent relative rotation between the coupling and the bone pin locking assembly when engaged. The coupling may also have a spring and a bore, the spring being at least partially accepted within the bore and compressed between the pin vise cooperating portion of the coupling and the bone pin locking assembly, to provide a force tending to separate the coupling and the bone pin locking assembly to allow free relative rotational movement during operation.

The coupling may further be configured to provide (i) rotation of the single-piece rod attachment member about a first axis substantially perpendicular to the longitudinal axis of the bone pin locking assembly, and (ii) rotation of the single-piece rod attachment member about the rod attachment member longitudinal axis, the longitudinal axis being substantially perpendicular to the first axis.

An external fixator may be provided for coupling bone pins to a bone fixation rod. The fixator may comprise a bone pin locking assembly comprising first and second engaging faces for engaging the bone pins, and may further comprise a fixation rod clamp, the clamp comprising a single-piece rod attachment member having a longitudinal axis, a jaw portion having first and second opposing jaws configured to receive the bone fixation rod, the first opposing jaw having a first spring constant and the second opposing jaw having a second spring constant, the first and second spring constants being unequal. The rod attachment member may further have a coupling portion, and the fixation rod clamp may have a coupling, the coupling having a pin vise cooperating portion to engage the bone pin locking assembly and configured to receive the coupling portion of the rod attachment member. The jaw portion of the rod attachment member may be configured to engage the bone fixation rod when the rod is pressed into the opposing jaws to thereby mechanically couple the bone pin locking assembly to the bone fixation rod. The coupling may also be configured to permit (i) rotation of the single-piece rod attachment member about a first axis substantially perpendicular to the bone pin locking assembly engaging faces, and (ii) rotation of the single-piece rod attachment member about the rod attachment member longitudinal axis, the rod attachment member longitudinal axis being substantially perpendicular to the first axis.

The external fixator pin vise portion first and second engaging faces may further comprise grooves, and the engaging faces may also be coupled with at least one threaded fastener. The pin vise portion may also be configured to permit engaging the bone pins through contact with the grooves of the engaging faces upon tightening of the at least one threaded fastener.

In an alternate embodiment, a fixation rod clamp for coupling a bone pin locking assembly to a bone fixation rod may be provided, the clamp comprising a single-piece rod attachment member comprising a jaw portion having a longitudinal axis and first and second opposing jaws configured to receive the bone fixation rod, and a coupling portion. The clamp may further comprise a coupling having a pin vise engaging portion to engage the bone pin locking assembly and configured to receive the coupling portion of the rod attachment member. The first opposing jaw may be associated with a first spring arm having a first wall and a first spring constant, and the second jaw may be associated with a second spring arm having a second wall and a second spring constant. The first and second spring constants may be unequal. The jaw portion of the rod attachment member may be configured to engage the bone fixation rod when the bone fixation rod is pressed into the opposing jaws to thereby mechanically couple the bone pin locking assembly to the bone fixation rod.

The fixation rod clamp my be configured so that when at least one of the first and second opposing jaws are displaced from a rest position, resulting spring forces are generated in the at least one spring arm which force the at least one jaw back to the rest position. The first spring arm first wall may have an outer surface and an inner surface, and the second wall may have an outer and an inner surface, and at least one surface may comprise a cutout. The at least one cutout may comprise a shape selected from the group consisting of arcuate, triangular, stepped and square shaped cutouts.

When the bone fixation rod is pressed into the rod attachment member, the first and second spring arms may be displaced an unequal amount. Likewise, when the bone fixation rod is pressed into the rod attachment member the first spring arm may be displaced and the second spring arm may remain substantially stationary. The first and second jaws may have a clearance therebetween sufficient to provide an interference between the opposing jaws and the bone fixation rod when the rod is pressed into the rod clamp jaw portion. The jaw portion may engage the fixation rod when the rod is pressed into the fixation rod clamp in a direction substantially along the longitudinal axis of the jaw portion.

The rod clamp may be configured to have a locked position which substantially prevents movement of the clamp along the bone fixation rod. A bolt may be disposed within and operatively associated with the jaw portion, such that tightening of the bolt locks the position of the assembly.

In an alternative embodiment, a fixation rod clamp may be provided for coupling first and second bone fixation rods, the clamp comprising first and second single-piece fixation rod attachment members, each member having a longitudinal axis and a jaw portion. The jaw portion may have first and second opposing jaws configured to receive the first or second bone fixation rod, the first opposing jaw having a first spring constant and the second opposing jaw having a second spring constant, the first and second spring constants being unequal. The first and second rod attachment members may each also have a coupling portion. The fixation rod clamp may have a coupling configured to receive the coupling portions of the first and second rod attachment members. The jaw portion of each rod attachment member may further be configured to engage a respective first or second bone fixation rod when the bone fixation rod is pressed into the opposing jaws to thereby mechanically couple the first and second bone fixation rods.

When the first or second opposing jaw of at least the first or second rod attachment members is displaced from a rest position, resulting spring forces may be generated in the at least one which force the at least one jaw back to the rest position. Further, when the first or second bone fixation rod is pressed into the respective rod attachment member the first and second opposing jaws may be displaced an unequal amount, or the first spring arm may be displaced and the second spring arm may remain substantially stationary.

The first and second opposing jaws of at least the first or second rod attachment member may have a clearance therebetween which is sufficient to provide an interference between the opposing jaws and the first or second bone fixation rod when the bone fixation rod is pressed into the fixation rod clamp jaw portion. The fixation rod clamp may be configured so that the jaw portion of at least the first or second rod attachment member engages the first or second bone fixation rod when the bone fixation rod is pressed into the fixation rod clamp in a direction substantially along the longitudinal axis of the rod attachment member. The clamp may further be configured to have a locked position which substantially prevents movement of the clamp along at least one of the bone fixation rods, and may also comprise a bolt disposed within the operatively associated with at least the first or second rod attachment member jaw portion, wherein tightening of the bolt configures the clamp to the locked position.

A method for treating a fractured bone is also disclosed, comprising the steps of percutaneously inserting at least one set of bone pins into the bone on a first side of a fracture; providing at least a first fixation rod clamp assembly comprising a single-piece fixation rod attachment member having a longitudinal axis, and a jaw portion having first and second opposing jaws configured to receive a bone fixation rod, the first opposing jaw having a first spring constant and the second opposing jaw having a second spring constant, the first and second spring constants being unequal, and a coupling portion, and a coupling comprising a pin vise cooperating portion to engage the bone pin locking assembly and configured to receive the coupling portion of the rod attachment member; engaging an external portion of at least one bone pin on the first side of the fracture in the pin vise portion of the first bone pin locking assembly; snapping the jaw portion of the single-piece fixation rod clamp onto the bone fixation rod in a direction substantially perpendicular to the longitudinal axis of the rod attachment member; adjusting the fixation rod clamp assembly to its final desired position and orientation; and immobilizing the at least first fixation rod clamp assembly along the bone fixation rod. The step of immobilizing the at least first fixation rod clamp assembly along the bone fixation rod may further be achieved by tightening a bolt disposed within the rod attachment member jaw portion.

BRIEF DESCRIPTION OF THE DRAWINGS

The features and advantages of the present invention will become more readily apparent from the following detailed description of the invention in which like elements are labeled similarly and in which:

FIGS. 5a, 5b and 5c are cross-sectional views of the embodiments of a rod attachment member of FIGS. 4a, 4b and 4c, and a bone fixation rod;

DETAILED DESCRIPTION OF THE PREFERRED EMBODIMENTS

The traumatological device of the present invention is discussed herein with reference to a preferred embodiment adapted to be used in the consolidation and fixation of a fractured long bone. It is to be understood that the invention finds applicability for use in any circumstance in which it is desired to fix the orientation of bone segments on either side of a fracture.

Figure 1A:
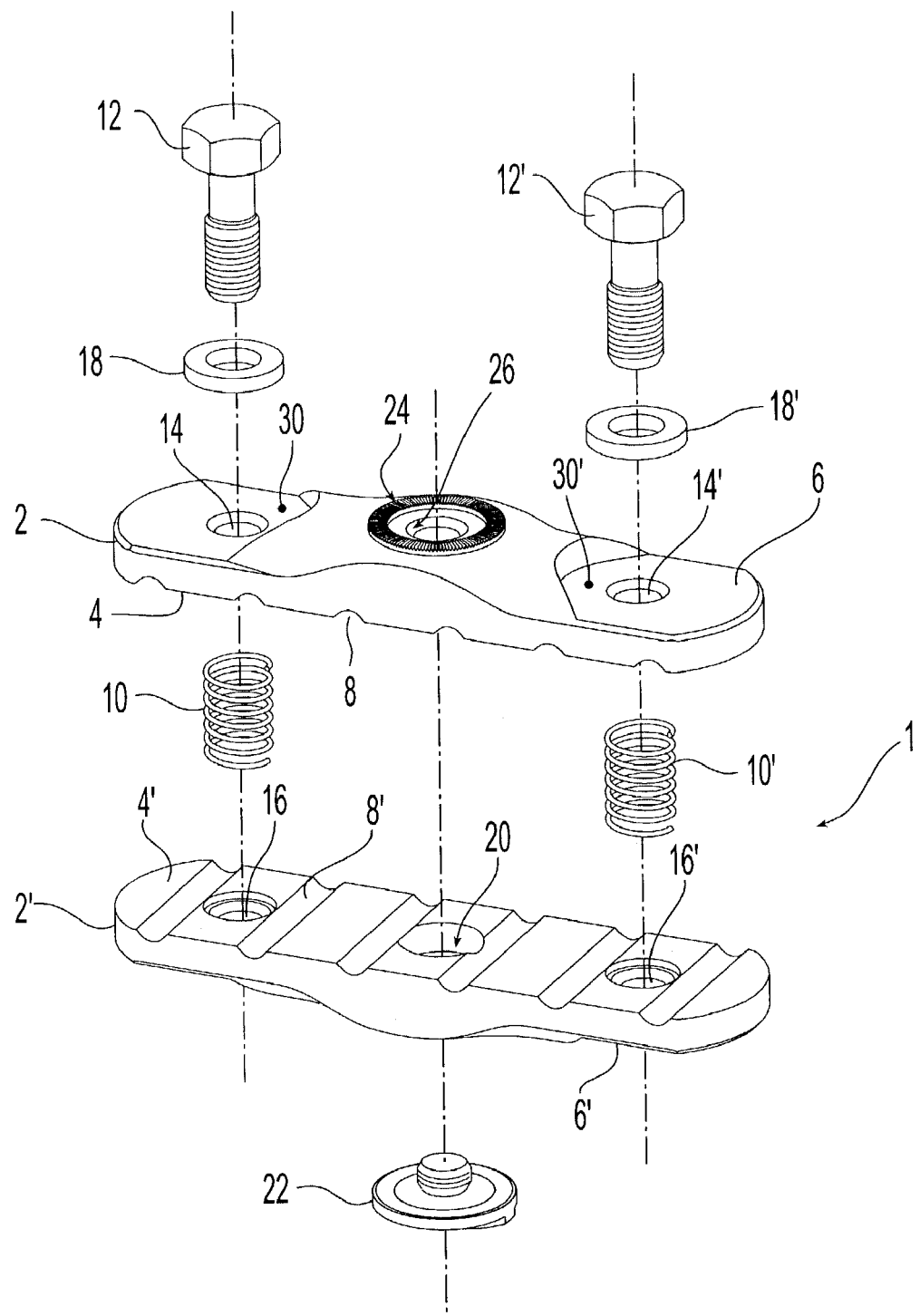
FIGS. 1A, 1B and 1C are two exploded perspective views of a bone pin vise portion, a bone pin vise opposing plate and star grind cover, and a bone pin vise opposing plate incorporating triangular bone pin clamping grooves, respectively, of the bone pin locking assembly of the current invention.
Figure 6:
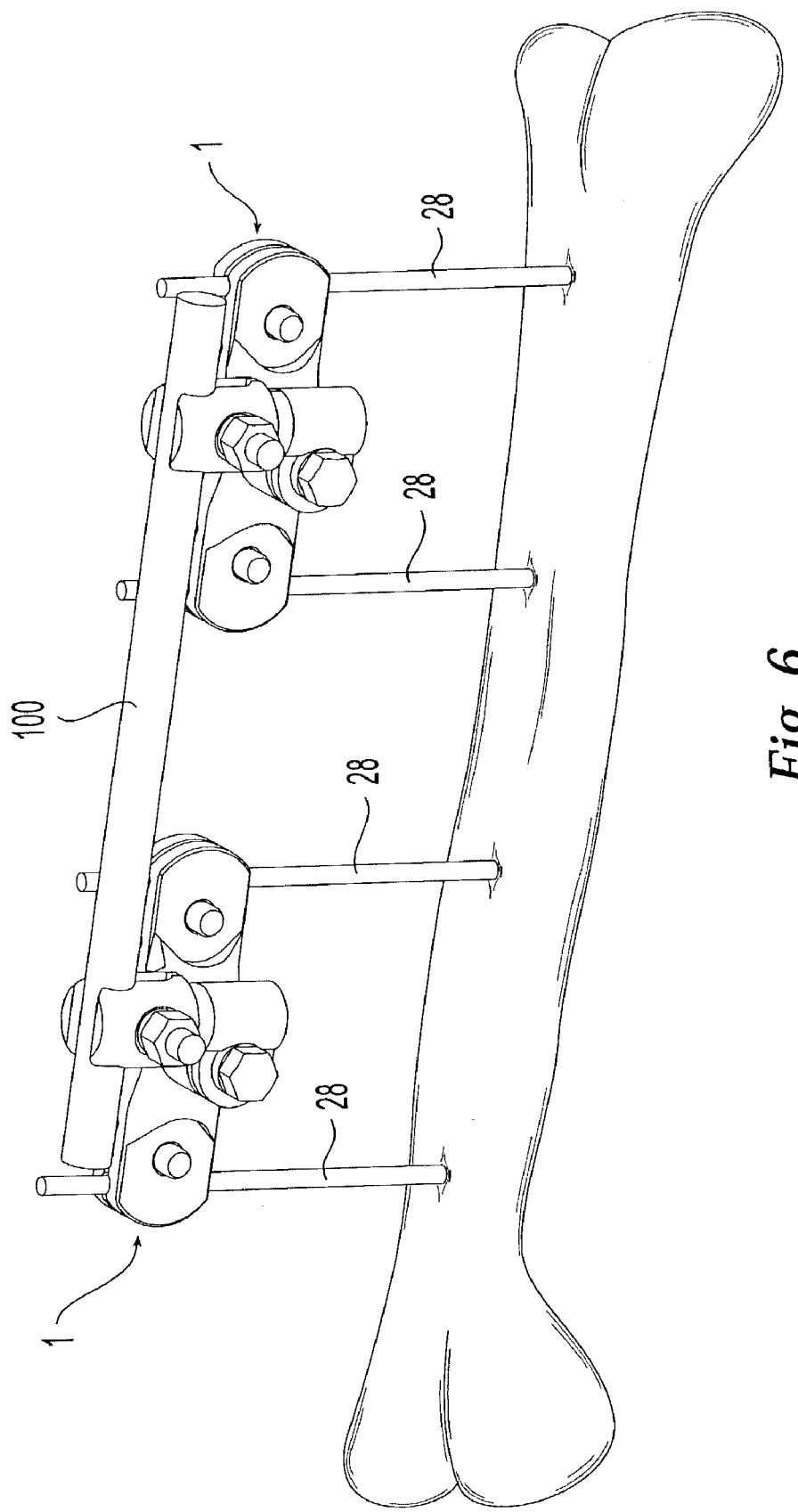
FIG. 6 is a perspective view of a one embodiment of a complete bone fixation device installed on a bone.

Referring more particularly to the drawings, FIG. 1a shows an exploded view of a bone pin vise portion. As shown in FIG. 1a, the bone pin vise portion 1 comprises first and second opposing plates 2 and 2' with engaging faces 4 and 4', and outside faces 6 and 6'. Each engaging face is characterized by a plurality of spaced parallel grooves 8 and 8' which are cylindrically arcuate and which are in confronting relation to the spaced parallel grooves on the face of the opposite plate. The parallel grooves 8 and 8' coordinate to receive the proximal ends of bone pins 28 (shown in FIG. 6) installed on one side of a fractured bone. When the pin vise portion is in the clamped condition, the bone pins 28 are nested in the respective grooves formed by the conjunction of parallel grooves 8 and 8' (of engaging faces 4 and 4'). It will be understood that the number and shape of the grooves is not critical to the operation of the device.

The opposing plates 2 and 2' are connected by two vise bolts 12 and 12' which operate to draw together engaging faces 4 and 4' in order to grip the proximal ends of bone pins 28 which have been installed in a bone. Vise bolts 12 and 12' are slideably accepted by corresponding bores 14 and 14' in each end of first opposing plate 2, and are threadably accepted by threaded bores 16 and 16' in each end of second opposing plate 2'. The internal threads of bores 16 and 16' of second opposing plate 2' correspond with the external threads of vise bolts 12 and 12' such that a clockwise rotation of vise bolts 12 and 12' acts to draw opposing plates 2 and 2', and therefore engaging faces 4 and 4', together. Further, first opposing plate 2 incorporates bolt head bearing surfaces 30 and 30' to provide uniform bearing contact with the bottoms of the heads of pin vice bolts 12 and 12'. The vise bolts 12 and 12' may be provided with washers 18 and 18' positioned between the heads of the vice bolts 12 and 12', and bolt head bearing surfaces 30 and 30' of the pin vise portion opposing plate 2. The washers serve to reduce friction between the vise bolts and bolt head bearing surfaces, thereby easing final tightening of the vise bolts.

Preferably, the vise bolts 12 and 12' will be initially fit with the washers 18 and 18', then installed in the opposing plates, followed by a "loose-fit" tightening to the point that only a small clearance remains between the cylindrical voids formed by the plurality of spaced parallel grooves 8 and 8' and the outside surfaces of the cylindrical bone pins 28. In this way the pin vise portion 1 may easily be slipped onto the bone pins 28, such that during the surgical procedure only minor additional tightening of the vise bolts 12 and 12' will be required to firmly fix the bone pins 28 within the bone pin vise portion 1.

Figure 3:
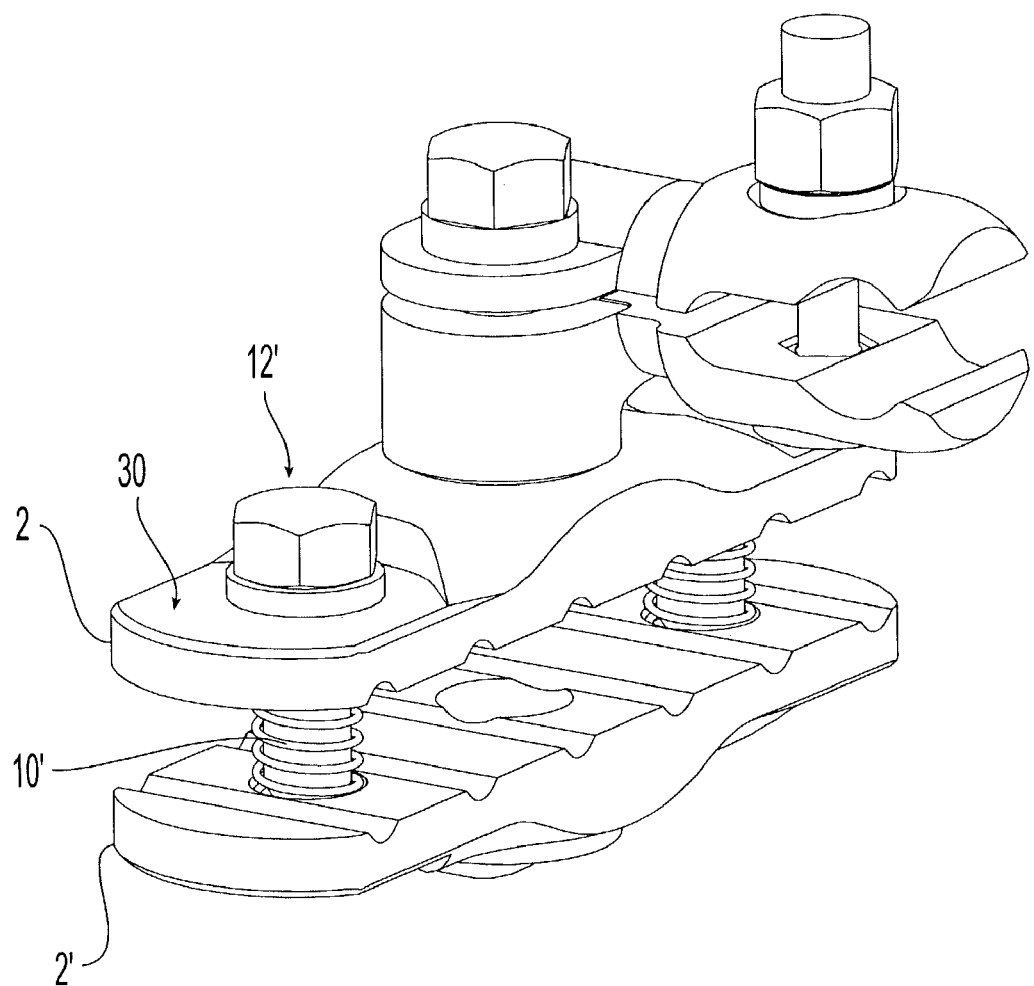
FIG. 3 is a perspective view of an assembled bone pin vise portion of FIG. 1 connected to an assembled fixation rod clamp of FIG. 2.

In a preferred embodiment, the pin vise portion opposing plates 2 and 2' incorporate coil springs 10 and 10' between engaging faces 4 and 4' to forcibly separate engaging faces 4 and 4'. The provision of this separating force holds the plates apart during installation of the pin vise portion onto the bone pin proximal ends, easing such installation. To this end, cylindrical coil springs 10 and 10' are installed about the shafts of vise bolts 12 and 12' such that vise bolt shafts are slidably received by the bore formed within the inside diameter of each coil spring 10 and 10' (see FIG. 3).

Figure 2:
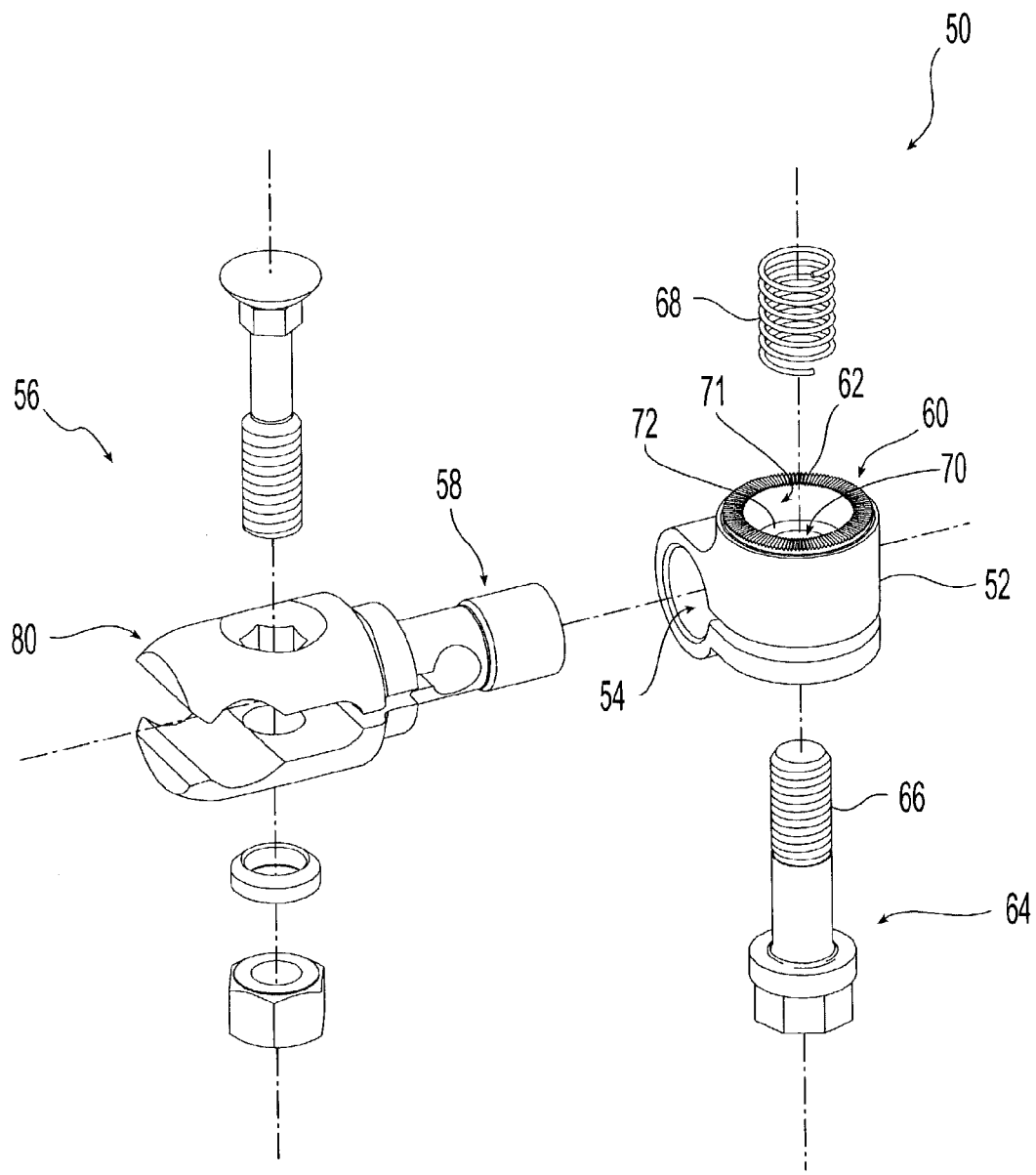
FIG. 2 is an exploded perspective view of a fixation rod clamp of the bone pin locking assembly of the current invention.

FIG. 2 shows an exploded view of one embodiment of a fixation rod clamp 50, comprising a single-piece rod attachment member 56, a coupling 52, a coil spring 68, and a coupling bolt 64. The single-piece rod attachment member has a cylindrical coupling portion 58 which is slidably disposed within an aperture 54 formed by the body of the coupling 52. Single-piece rod attachment member 56 is thus interconnected to and slidably disposed within the coupling 52 so as to allow 360-degree rotation of the single-piece rod attachment member 56 within the coupling aperture 54. The coupling bolt 64, having a head and a threaded distal end 66, is slidably disposed within a bore 70 formed in the body of coupling 52. The longitudinal axis of bore 70 is oriented perpendicular to that of the coupling aperture 54. The coupling bolt threaded distal end 66 is threadably accepted by an internally and compatibly threaded bore 26 formed in the top center of opposing plate 2 (shown in FIG. 1a) of pin vise portion 1 (shown in FIG. 1a). The single-piece rod attachment member 56 is interconnected to and rotatably disposed, with two degrees of rotational freedom, about pin vise portion 1, and about bone pins 28 (shown in FIG. 6). The first degree of rotational freedom is provided by the rotation of single-piece rod attachment member 56 relative to the fixation rod clamp coupling 52; the second degree of rotational freedom is provided by the rotation of the fixation rod clamp coupling relative to pin vise portion 1.

The single-piece rod attachment member 56 is stabilized and fixed to the fixation rod clamp coupling 52 by tightening the coupling bolt 64. Tightening of the coupling bolt 64 also results in the stabilization and fixation of the entire fixation rod clamp 50 to the pin vise portion 1.

In a preferred embodiment, the coupling 52 has a bearing face 60 incorporating serrations 62 which extend over the entire face, and which correspond with like serrations 24 (shown in FIG. 1a) formed in the corresponding bearing face of the pin vise portion 1. The serrations may be disposed in a radial fashion to form a "star grind," or may have any type of profile known in the art. The serrations 62, 24 serve to minimize or prevent rotational slippage between the coupling 52 and the pin vise portion 1 subsequent to final tightening of the coupling bolt 64

Figure 1B:
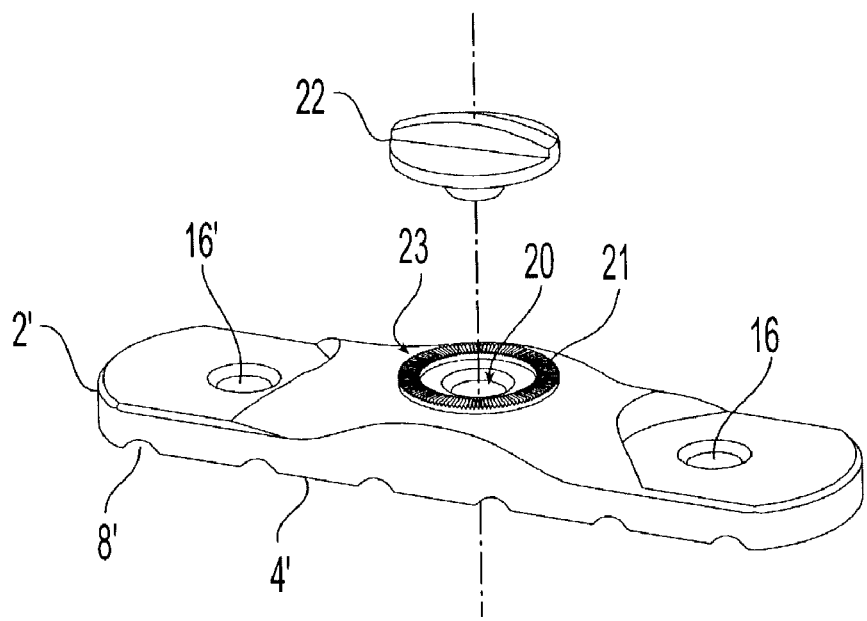
Figure 1C:
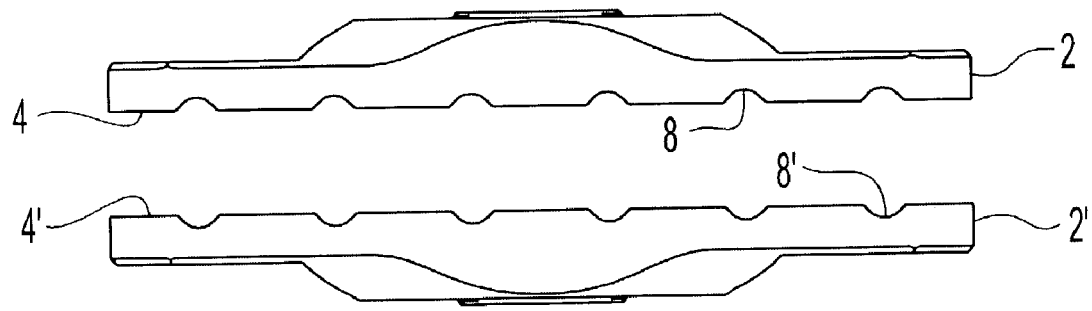

In another preferred embodiment, the pin vise portion opposing plate 2' (shown in FIG. 1*b*) incorporates an internally threaded bore 20, into which the coupling bolt 64 of a second fixation rod clamp 50 (shown in FIG. 2) may be threaded. The bearing face 21 of the pin vise portion opposing plate 2' incorporates serrations 23 which extend over the entire face, and which correspond with like serrations 62 of the bearing face 60 of a second fixation rod clamp 50 (shown in FIG. 2). The serrations 62, 23 serve to minimize or prevent rotational slippage between the second coupling 52 and the pin vise portion 1 subsequent to final tightening of the second coupling bolt 64. Two fixation rod clamps 50 may thereby be installed on one pin vise portion 1 to provide the fracture site with the additional stabilizing force of a second bone fixation rod 100 (shown in FIG. 7). For those instances in which the surgeon does not require the additional stabilizing force of a second bone fixation rod, an externally threaded "star grind" cover 22 (shown in FIGS. 1*a* and 1*b*) is provided. The cover is threadably accepted by the internally threaded bore 20 of the pin vise portion opposing plate 2' (shown in FIGS. 1*a* and 1*b*).

As shown in FIG. 2, the coupling bolt 64 may be provided with a coil spring 68 disposed about the circumference of the bolt 64. The spring is partially slidably received within a bore 71 provided in the coupling bearing face 60. This bore is of larger diameter than coupling bore 70, which results in the creation of a circumferential ledge 72 within the coupling 52. When compressed between the coupling circumferential ledge 72 and the pin vise portion 1 (shown in FIG. 1*a*), the spring 68 acts to provide a force tending to separate the coupling 52 and the pin vise portion 1. This force prevents engagement of the serrations 62, 24 during installation, and thus enables easy relative rotation and fit-up.

Figure 4A:
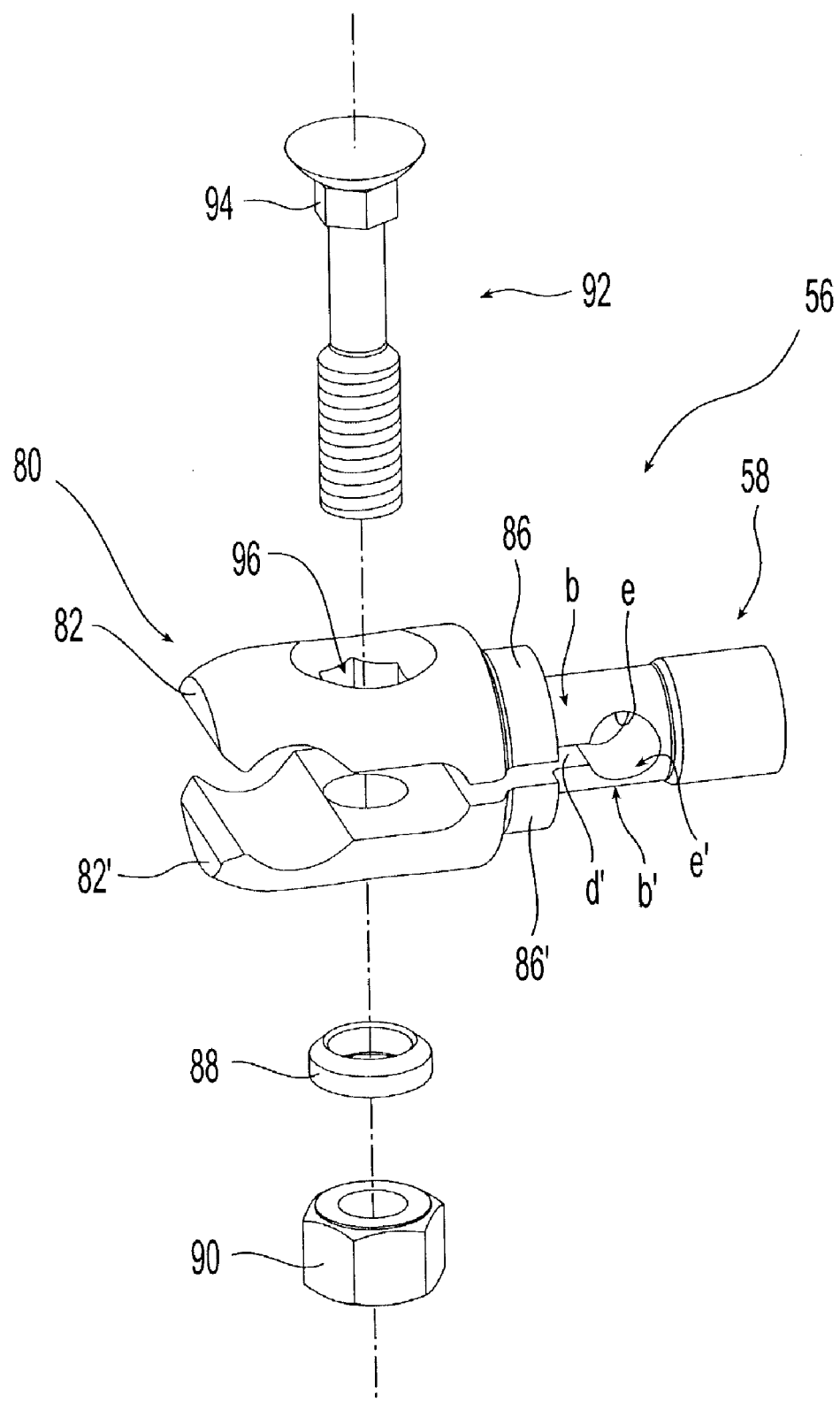
FIGS. 4a, 4b and 4c are exploded perspective views of three embodiments of a rod attachment member.
Figure 5A:
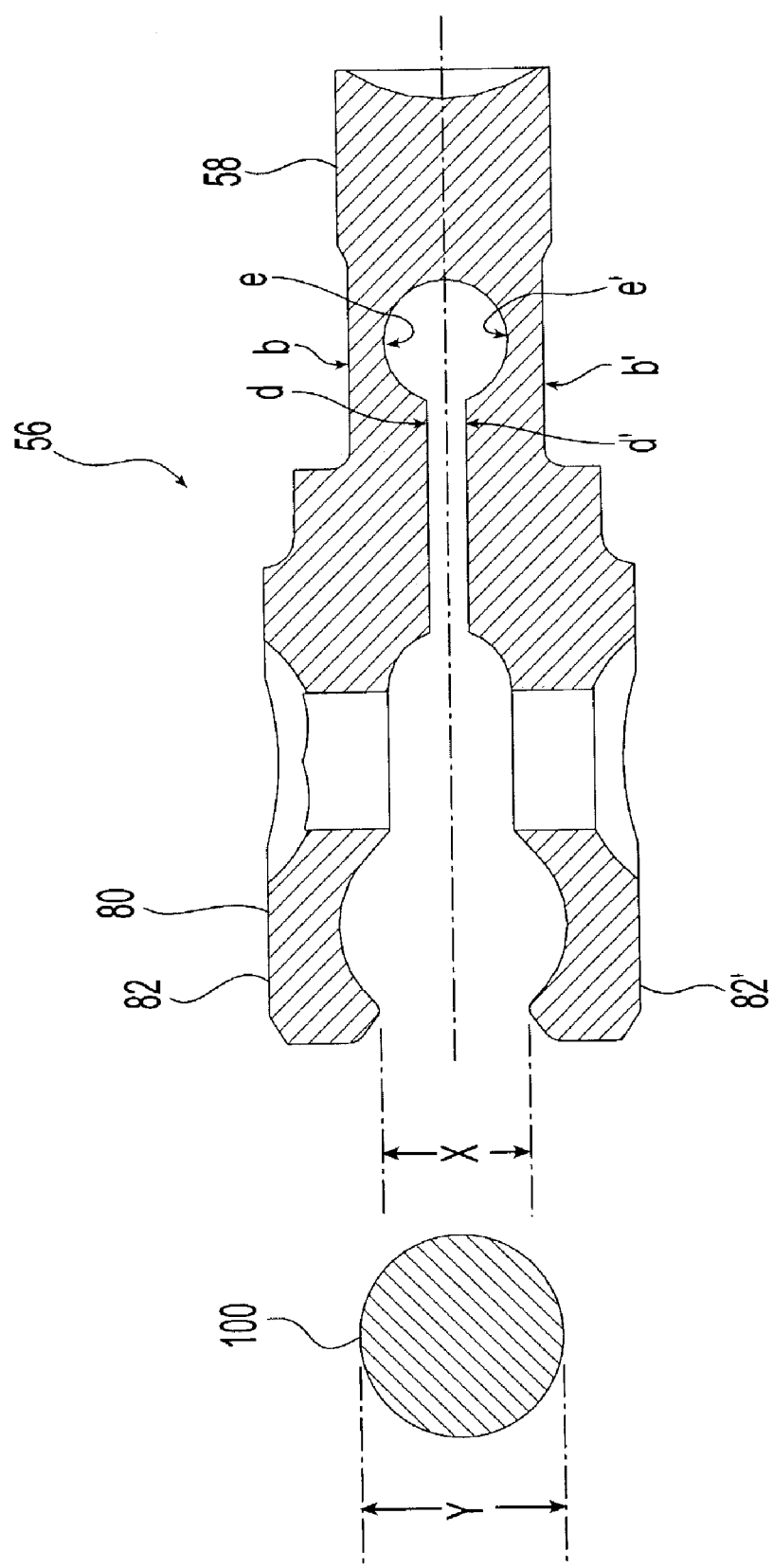

FIG. 4*a* shows the details of one embodiment of the novel single-piece rod attachment member 56 of the present invention. The single-piece rod attachment member comprises a jaw portion 80, which further comprises a set of opposing jaws 82 and 82', each associated with a respective spring arm 86 and 86'. The spring arms converge to a smooth cylindrical coupling portion 58. Significantly, the rod attachment member 56 is manufactured in a single piece, so that when the jaws 82 and 82' are positively displaced with respect to their rest position, a resulting spring force is generated which tends to force the jaws back to the rest position. The jaw portion 80 is preferably manufactured such that the initial clearance "X" between opposing jaws 82 and 82' is slightly smaller than the outside diameter "Y" of the bone fixation rod 100 (shown in FIGS. 5*a*, 5*b* and 5*c*). In this way an interference is established between jaws 82 and 82' and the bone fixation rod 100 when the bone fixation rod is initially installed into the jaw portion 80. Based on the natural spring action of the spring arms 86 and 86' adjoining the jaws 82 and 82' respectively, the relative interference between the jaws and the bone fixation rod enables the bone fixation rod 100 to be snapped into the bone pin locking assembly (comprising pin vise portion 1 and fixation rod clamp 50) by the operator, resulting in the capture of the bone fixation rod 100 within the jaw portion 80. Although not fully stabilized, the spring action of the spring arms is sufficient to maintain a loose coupling of the assembly with the rod. This frees up the hands of the surgeon performing the fixation procedure.

In one embodiment the spring arms 86, 86' each may have an outer surface b, b' and an inner surface d, d', and at least one of the inner surfaces may have a cutout e, e' to reduce the force required to snap the bone fixation rod 100 into the rod attachment member jaw portion 80. The cutout(s) may be arcuate, or may be any other geometric shape appropriate to reduce the thickness of at least one or perhaps both of the spring arms. The cutout(s) may be formed by any acceptable method (e.g. machining, forming, casting, etc.). Furthermore, cutouts e, e' may be symmetrical, providing spring arms with essentially equal spring constants, or they may be asymmetrical so as to provide spring arms with different spring constants. Additionally, the groove defined by the space between inner surfaces d and d' may be centered about the longitudinal axis of the single-piece rod attachment member, providing spring arms with essentially equal spring constants, or it may be offset so as to provide spring arms having different spring constants.

Final stabilization of the bone fixation rod 100 within the jaw portion 80 is accomplished through the use of a bolt 92 placed through the jaw portion spring arms 86 and 86', in combination with a nut 90 (see FIG. 4*a*). Upon tightening the nut 90 and bolt 92, the spring arms 86 and 86', and most importantly for the purposes of the invention, the adjoining jaws 82 and 82', are drawn together until the bone fixation rod 100 is firmly held between the jaws 82 and 82'. Repeated loosening and tightening of the fixation rod clamp on the bone fixation rod is possible without the need for re-engagement of the rod within the jaw. In this way the surgeon may easily and repeatedly adjust the position of the fixation rod clamp along the bone fixation rod.

An external hexagon 94 may be provided integral to the shoulder of the jaw bolt 92. This external hexagon 94 conforms to an internal hexagonal recess 96 provided within jaw portion spring arm 86. The bolt is thereby rotationally fixed to the jaw portion, such that the surgeon need only focus on threading the nut onto the bolt without having to worry about holding the bolt still.

A washer 88 may be provided between the nut 90 and jaw portion spring arm 86'. This washer can be of any design known in the art satisfactory to prevent galling of the nut and jaw portion spring arm, and to facilitate installation of nut 90 and bolt 92.

Figure 4C:
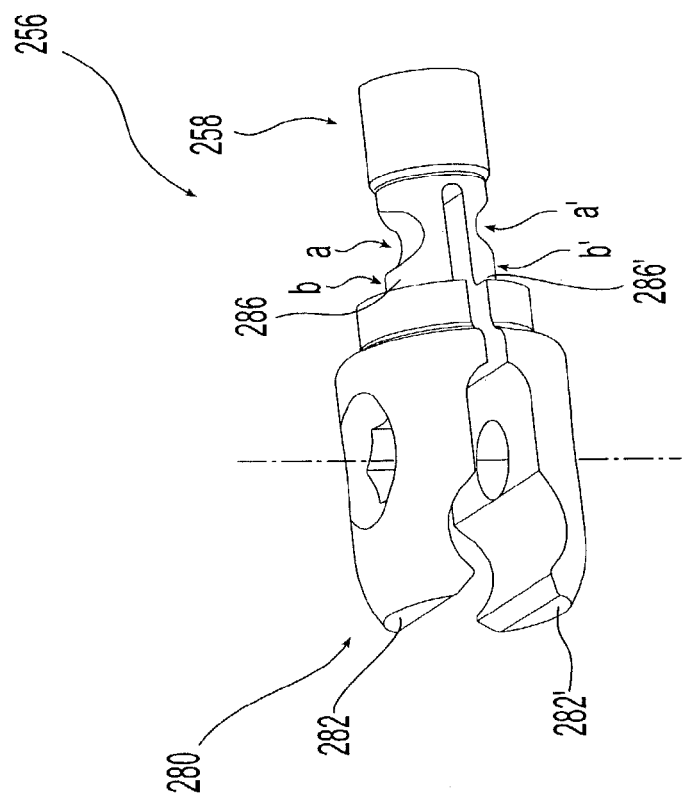
Figure 4B:
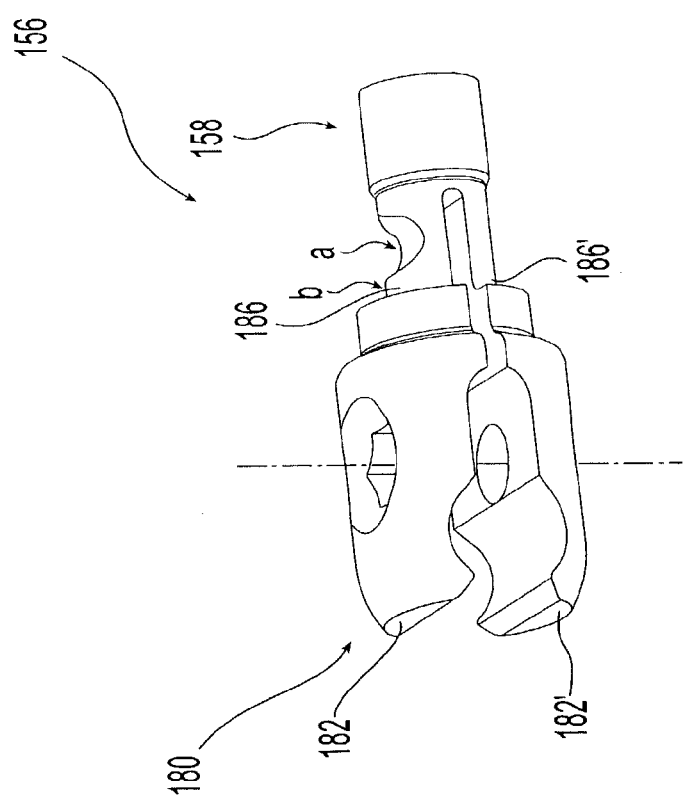

FIG. 4*b* shows the details of another embodiment of the single piece rod attachment member 156 of the present invention. The single piece rod attachment member of this embodiment comprises a jaw portion 180, which further comprises a set of opposing jaws 182 and 182', each associated with a respective spring arm 186 and 186'. The spring arms converge to a smooth cylindrical coupling portion 158. Spring arm 186 incorporates an arcuate cutout "a" which runs across outside surface "b." The cutout forms a trough whose centerline is perpendicular to the longitudinal axis of the rod attachment member 156. The arcuate cutout "a" reduces the wall thickness "c" of spring arm 186 (shown in FIG. 5*b*), so that thickness "c" is less than the corresponding wall thickness "c'" of spring arm 186'. This reduction in thickness renders the spring constant for spring arm 186 smaller than the spring constant for spring arm 186', such that when equal force is applied to the jaws 182, 182', such as during initial installation of rod 100 (shown in FIG. 5*b*), jaw 182 will be displaced an amount significantly greater than jaw 182'. In a further embodiment, spring arm thickness "c" is sufficiently smaller than spring arm thickness "c'" that when equal force is applied to the jaws, such as during initial installation of rod 100 in jaw portion 180, jaw 182 is displaced from its rest position an amount sufficient to accept rod 100 in jaw portion 180. Because of the differing geometries of the spring arms, jaw 182' will be displaced by an amount much less than jaw 182, such that it will effectively remain stationary. This differs from the embodiment described above (shown in FIG. 4*a*) in which the spring arm geometries are essentially the same, resulting in the displacement of both spring arms by an equal amount. The overall strength of the spring arms 186, 186' may be maintained, or even increased, as compared to the embodiment described above and in FIG. 4a, by increasing the overall cross-section of the spring arms, such as by making the spring arms wider.

FIG. 4c shows the details of a further embodiment of the single piece rod attachment member 256 of the present invention. The single piece rod attachment member of this embodiment comprises a jaw portion 280, which further comprises a set of opposing jaws 282 and 282', each associated with a respective spring arm 286 and 286'. The spring arms converge to a smooth cylindrical coupling portion 258. Spring arms 286, 286' each incorporate an arcuate cutout "a," "a'" which runs across outside surface "b," "b'." Each cutout forms a trough whose centerline is perpendicular to the longitudinal axis of the rod clamp 256. The arcuate cutouts "a," "a'" reduce the wall thickness "c," "c'" of spring arms 286, 286', thereby reducing the corresponding spring constants of the spring arms. The force required to install rod 100 (shown in FIG. 5c) in jaw portion 280 of the rod clamp 256, is therefore reduced as compared to the force required to install the rod on a jaw portion whose spring arms incorporate no such outer surface cutouts (see FIG. 4a) or where only one spring arm has a cutout (see FIG. 4b). Where cutouts a, a' are equal, the operation of this embodiment is similar to that described above in reference to FIG. 4a, as both spring arms 286, 286' will be displaced by an equal amount upon initial installation of the bone fixation rod. As with the embodiment discussed above in reference to FIG. 4b, the overall strength of the spring arms 286, 286' may be maintained, or even increased, as compared to the embodiment described above in reference to FIG. 4a, again by increasing the overall cross-section of the spring arms such as by making the spring arms wider. Cutouts a, a' may, in an alternate embodiment, be of different size or shape, providing spring arms 286, 286 with unequal spring constants.

It is noted that in addition to the arcuate cutouts "a," "a'" depicted in FIGS. 4b and 4c, numerous other configurations may be employed to produce spring arms which flex varying amounts during installation of the fixation rod 100, for example, providing spring arms having different geometric shapes and/or widths, spring arms incorporating stepped thicknesses, or combinations of single or multiple interior or exterior cutouts.

Figure 7:
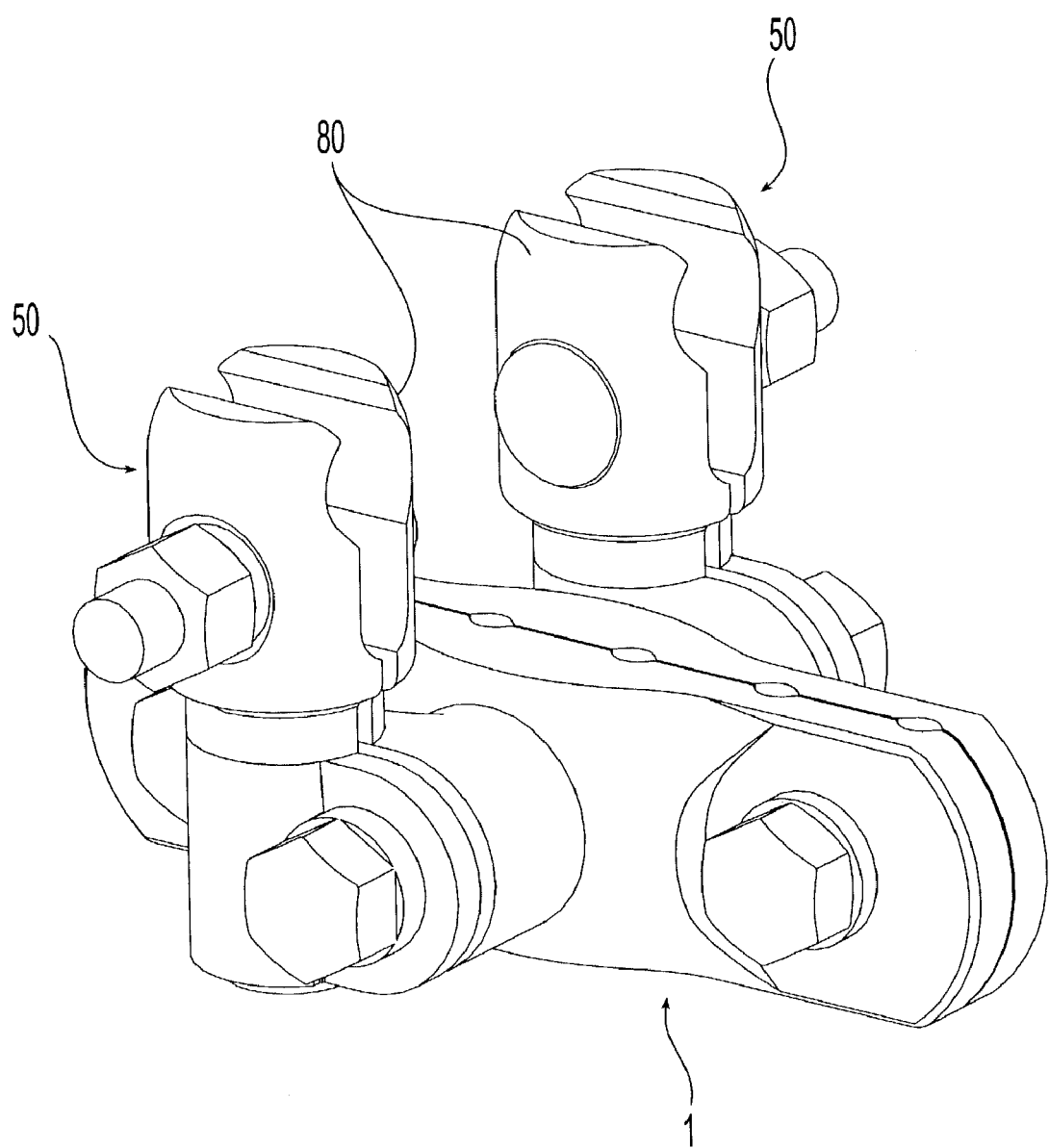
FIG. 7 is a perspective view of an embodiment of the stacked clamp assembly of the present invention.

FIG. 7 shows a "stacked" bone pin locking assembly which comprises one pin vise portion 1 with two associated fixation rod clamps 50. Such a stacked assembly permits the surgeon to provide an additional stabilizing force, connected to a second bone fixation rod 100, to the fracture site. In this way a framework of bone fixation rods may be built about the fracture site.

Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A fixation rod clamp for coupling a bone pin locking assembly to at least a first bone fixation rod, the clamp comprising:
   at least a first single-piece rod attachment member having:
   a longitudinal axis,
   a jaw portion having first and second opposing jaws configured to receive the bone fixation rod, the first opposing jaw having a first spring constant and the second opposing jaw having a second spring constant, the first and second spring constants being unequal, and
   a coupling portion extending from the jaw portion; and
   a coupling having a pin vise cooperating portion to engage the bone pin locking assembly and configured to receive the coupling portion of the rod attachment member,
   wherein the jaw portion of the rod attachment member is configured to engage the bone fixation rod when the bone fixation rod is pressed into the opposing jaws to thereby mechanically couple the bone pin locking assembly to the bone fixation rod.

2. The fixation rod clamp of claim 1, wherein when at least one of the first and second opposing jaws is displaced from a rest position, a resulting spring force is generated in the at least one jaw which forces the jaw back to the rest position.

3. The fixation rod clamp of claim 1, wherein when the bone fixation rod is pressed into the rod attachment member the first and second jaws are displaced an unequal amount.

4. The fixation rod clamp of claim 2, wherein when the bone fixation rod is pressed into the rod attachment member the first jaw is displaced from its rest position and the second jaw remains substantially stationary.

5. The fixation rod clamp of claim 1, wherein the first and second opposing jaws have a clearance therebetween which is sufficient to provide an interference between the opposing jaws and the bone fixation rod when the bone fixation rod is pressed into the fixation rod clamp jaw portion.

6. The fixation rod clamp of claim 1, wherein the clamp is configured to have a locked position which substantially prevents movement of the clamp along the bone fixation rod.

7. The fixation rod clamp of claim 6, further comprising a bolt disposed within and operatively associated with the fixation rod clamp jaw portion, wherein tightening of the bolt configures the clamp to the locked position.

8. The fixation rod clamp of claim 1, wherein the jaw portion engages the bone fixation rod when the bone fixation rod is pressed into the fixation rod clamp in a direction substantially along the longitudinal axis of the rod attachment member.

9. The fixation rod clamp of claim 1, wherein the pin vise cooperating portion of the coupling comprises a bearing face incorporating serrations configured to cooperatively engage serrations in the bone pin locking assembly, the serrations configured upon their engagement to prevent relative rotational movement between the coupling and the bone pin locking assembly.

10. The fixation rod clamp of claim 1, wherein the coupling further comprises a spring and a bore, wherein the spring is at least partially accepted within the bore and compressed between the pin vise cooperating portion of the coupling and the bone pin locking assembly, and provides a force tending to separate the coupling and the bone pin locking assembly to allow free relative rotational movement during operation.

11. The fixation rod clamp of claim 1, wherein the coupling is configured to provide (i) rotation of the single piece rod attachment member about a first axis substantially perpendicular to the longitudinal axis of the bone pin locking assembly, and (ii) rotation of the single piece rod attachment member about the rod attachment member longitudinal axis, the rod attachment member longitudinal axis being substantially perpendicular to the first axis.

12. An external fixator for coupling bone pins to a bone fixation rod comprising:
 a bone pin locking assembly comprising first and second engaging faces for
 engaging the bone pins, and the fixation rod clamp of claim 1;
 wherein the coupling is configured to permit: (i) rotation of the single-piece rod attachment member about a first axis substantially perpendicular to the bone pin locking assembly engaging faces, and (ii) rotation of the single-piece rod attachment member about the rod attachment member longitudinal axis, the rod attachment member longitudinal axis being substantially perpendicular to the first axis.

13. The external fixator of claim 12, wherein the pin vise portion first and second engaging faces comprise grooves, and wherein the engaging faces are coupled with at least one threaded fastener, and wherein the pin vise portion is configured to permit engaging the bone pins through contact with the grooves of the first and second engaging faces upon tightening of the at least one threaded fastener.

14. A fixation rod clamp for coupling a bone pin locking assembly to a bone fixation rod, the clamp comprising:
 a single-piece rod attachment member comprising:
  a jaw portion having a longitudinal axis and first and second opposing
  jaws configured to receive the bone fixation rod, and
  a coupling portion extending from the jaw portion; and
 a coupling having a pin vise cooperating portion to engage the bone pin locking assembly and configured to receive the coupling portion of the rod attachment member,
 wherein the first opposing jaw is associated with a first spring arm having a first wall and a first spring constant, and the second opposing jaw is associated with a second spring arm having a second wall and a second spring constant, the first and second spring constants being unequal, and wherein the jaw portion of the rod attachment member is configured to engage the bone fixation rod when the bone fixation rod is pressed into the opposing jaws to thereby mechanically couple the bone pin locking assembly to the bone fixation rod.

15. The fixation rod clamp of claim 14, wherein when at least one of the first and second opposing jaws are displaced from a rest position, resulting spring forces are generated in the at least one spring arm which force the at least one jaw back to the rest position.

16. The fixation rod clamp of claim 14, wherein the first wall has an outer surface and an inner surface, and the second wall has an outer surface and an inner surface, and wherein at least one surface comprises a cutout.

17. The fixation rod clamp of claim 16, wherein the at least one cutout comprises a shape selected from the group consisting of arcuate, triangular, stepped and square shaped cutouts.

18. The fixation rod clamp of claim 14, wherein when the bone fixation rod is pressed into the rod attachment member the first and second spring arms are displaced an unequal amount.

19. The fixation rod clamp of claim 14, wherein when the bone fixation rod is pressed into the rod attachment member the first spring arm is displaced and the second spring arm remains substantially stationary.

20. The fixation rod clamp of claim 14, wherein the first and second opposing jaws have a clearance therebetween which is sufficient to provide an interference between the opposing jaws and the bone fixation rod when the bone fixation rod is pressed into the fixation rod clamp jaw portion.

21. The fixation rod clamp of claim 14, wherein the jaw portion engages the bone fixation rod when the bone fixation rod is pressed into the fixation rod clamp in a direction substantially along the longitudinal axis of the jaw portion.

22. The fixation rod clamp of claim 14, wherein the clamp is configured to have a locked position which substantially prevents movement of the clamp along the bone fixation rod.

23. The fixation rod clamp of claim 22, further comprising a bolt disposed within and operatively associated with the fixation rod clamp jaw portion, wherein tightening of the bolt locks the position of the assembly.

24. The fixation rod clamp of claim 1 for coupling the first bone fixation rod and a second bone fixation rod, the clamp comprising:
 a second single-piece fixation rod attachment member, the second rod attachment member having:
  a longitudinal axis,
  a jaw portion having first and second opposing jaws configured to receive the second bone fixation rod, the first opposing jaw having a first spring constant and the second opposing jaw having a second spring constant, the first and second spring constants being unequal, and
  a coupling portion; and
 a coupling configured to receive the coupling portions of the first and second rod attachment member,
 wherein the jaw portion of the second rod attachment member is configured to engage the second bone fixation rod when the second bone fixation rod is pressed into the opposing jaws to thereby mechanically couple the first and second bone fixation rods.

25. The fixation rod clamp of claim 24, wherein when at least the first or second opposing jaw of at least the first or second rod attachment member is displaced from a rest position, resulting spring forces are generated in the at least one jaw which force the at least one jaw back to the rest position.

26. The fixation rod clamp of claim 24 wherein when the first or second bone fixation rod is pressed into the respective rod attachment member the first and second opposing jaws are displaced an unequal amount.

27. The fixation rod clamp of claim 24 wherein when the first or second bone fixation rod is pressed Into the respective rod attachment member the first spring arm is displaced and the second spring arm remains substantially stationary.

28. The fixation rod clamp of claim 24 wherein the first and second opposing jaws of at least the first or second rod attachment member have a clearance therebetween which is sufficient to provide an interference between the opposing jaws and the first or second bone fixation rod when the bone fixation rod is pressed into the fixation rod clamp jaw portion.

29. The fixation rod clamp of claim 24 wherein the jaw portion of at least the first or second rod attachment member engages the first or second bone fixation rod when the bone fixation rod is pressed into the fixation rod clamp in a direction substantially along the longitudinal axis of the rod attachment member.

30. The fixation rod clamp of claim 24, wherein the clamp is configured to have a locked position which substantially prevents movement of the clamp along at least one of the bone fixation rods.

31. The fixation rod clamp of claim 30 further comprising a bolt disposed within and operatively associated with at least the first or second rod attachment member jaw portion, wherein tightening of the bolt configures the clamp to the locked position.

* * * * *